(12) United States Patent
Carlsson et al.

(10) Patent No.: US 9,981,252 B2
(45) Date of Patent: May 29, 2018

(54) CATALYST PREPARATION METHOD

(71) Applicant: Johnson Matthey PLC, London (GB)

(72) Inventors: Mikael Per Uno Carlsson, Cleveland (GB); Jonathan Geoffrey Oliver, Sunderland (GB); Mark Robert Feaviour, Reading (GB); David James Birdsall, Cleveland (GB); Samuel Arthur French, Neasham (GB)

(73) Assignee: Johnson Matthey PLC, London, England (GB)

( * ) Notice: Subject to any disclaimer, the term of this patent is extended or adjusted under 35 U.S.C. 154(b) by 0 days. days.

(21) Appl. No.: 15/279,964

(22) Filed: Sep. 29, 2016

(65) Prior Publication Data
US 2017/0014809 A1    Jan. 19, 2017

Related U.S. Application Data

(62) Division of application No. 13/318,273, filed as application No. PCT/GB2010/050624 on Apr. 15, 2010, now Pat. No. 9,480,971.

(30) Foreign Application Priority Data

May 1, 2009 (GB) .................................. 0907539.1

(51) Int. Cl.
*B01J 23/02* (2006.01)
*B01J 23/78* (2006.01)
(Continued)

(52) U.S. Cl.
CPC ............. *B01J 23/78* (2013.01); *B01J 23/002* (2013.01); *B01J 23/02* (2013.01); *B01J 35/008* (2013.01);
(Continued)

(58) Field of Classification Search
USPC ........................................ 502/341, 100, 300
See application file for complete search history.

(56) References Cited

U.S. PATENT DOCUMENTS 4,090,980 A    5/1978    Carter et al.
4,329,530 A    5/1982    Irvine et al.
(Continued)

FOREIGN PATENT DOCUMENTS

WO    WO-2004/014549 A1    2/2004
WO    WO-2006/016983 A2    2/2006
(Continued)

OTHER PUBLICATIONS

International Preliminary Report on Patentability dated Apr. 30, 2013, from PCT International App. No. PCT/GB2011/051889.
(Continued)

*Primary Examiner* — James E McDonough
(74) *Attorney, Agent, or Firm* — Baker & Hostetler LLP

(57) ABSTRACT

A method for preparing a catalyst comprising (i) preparing a calcined shaped calcium aluminate catalyst support, (ii) treating the calcined shaped calcium aluminate support with water, and then drying the support, (iii) impregnating the dried support with a solution containing one or more metal compounds and drying the impregnated support, (iv) calcining the dried impregnated support, to form metal oxide on the surface of the support and (v) optionally repeating steps (ii), (iii) and (iv) on the metal oxide coated support. The method provides an eggshell catalyst in which the metal oxide is concentrated in an outer layer on the support.

18 Claims, 1 Drawing Sheet

(51) Int. Cl.
    *B01J 23/00*     (2006.01)
    *B01J 35/00*     (2006.01)
    *B01J 35/02*     (2006.01)
    *B01J 37/00*     (2006.01)
    *C01B 3/38*     (2006.01)
    *C01B 3/40*     (2006.01)
    *C07C 1/04*     (2006.01)

(52) U.S. Cl.
CPC ......... *B01J 35/026* (2013.01); *B01J 37/0009* (2013.01); *C01B 3/38* (2013.01); *C01B 3/40* (2013.01); *C07C 1/04* (2013.01); *C01B 2203/0233* (2013.01); *C01B 2203/062* (2013.01); *C01B 2203/1011* (2013.01); *C01B 2203/1047* (2013.01); *C01B 2203/1052* (2013.01); *C01B 2203/1058* (2013.01); *C01B 2203/1076* (2013.01); *C01B 2203/1082* (2013.01); *C01B 2203/1241* (2013.01); *C01B 2203/1252* (2013.01); *Y02P 20/52* (2015.11)

(56) References Cited

U.S. PATENT DOCUMENTS

| | | | |
|---|---|---|---|
| 4,380,589 A | | 4/1983 | Murchison et al. |
| 4,707,351 A | * | 11/1987 | Lord ........................ B01J 23/74 |
| | | | 106/692 |
| 4,906,603 A | | 3/1990 | Burgfels et al. |
| 2008/0032887 A1 | | 2/2008 | Ratnasamy et al. |

FOREIGN PATENT DOCUMENTS

| | | |
|---|---|---|
| WO | WO-2010/029323 A1 | 3/2010 |
| WO | WO-2010/029324 A1 | 3/2010 |
| WO | WO-2010/125369 A2 | 11/2010 |

OTHER PUBLICATIONS

International Preliminary Report on Patentability dated Nov. 1, 2011, from PCT International Application No. PCT/GB2010/050624.
International Search Report dated Feb. 4, 2011, from PCT International Application No. PCT/GB2010/050624.
International Search Report dated Feb. 8, 2012, from PCT International Application No. PCT/GB2011/051889.
Office Action for Chinese Patent Application No. 201180052096.0, dated Jul. 1, 2014.
Song et al., Industrial Catalysis, vol. 12, No. (8) 7 pages (2004).
Vagia et al., Applied Catalysis A: General, 351(1):111-21 (2008).
Entire prosecution history of U.S. Appl. No. 13/881,933, filed Jul. 15, 2013, entitled "Catalyst Preparation Method."
Entire prosecution history of U.S. Appl. No. 15/258,090, filed Sep. 7, 2016, entitled "Catalyst Preparation Method."

* cited by examiner

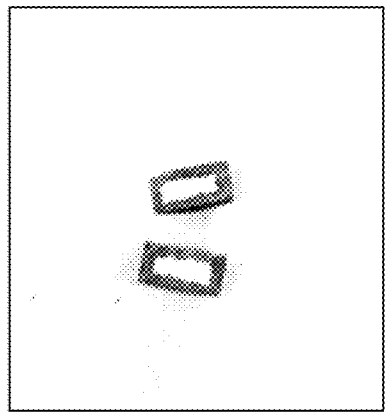
Figure 1
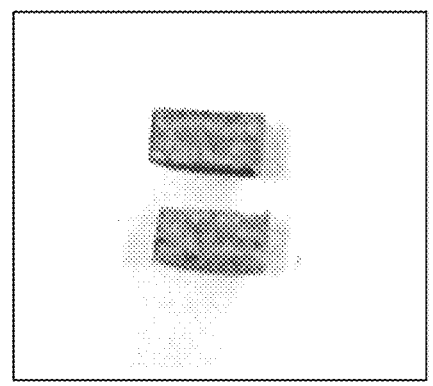
Figure 2 (Comparative)
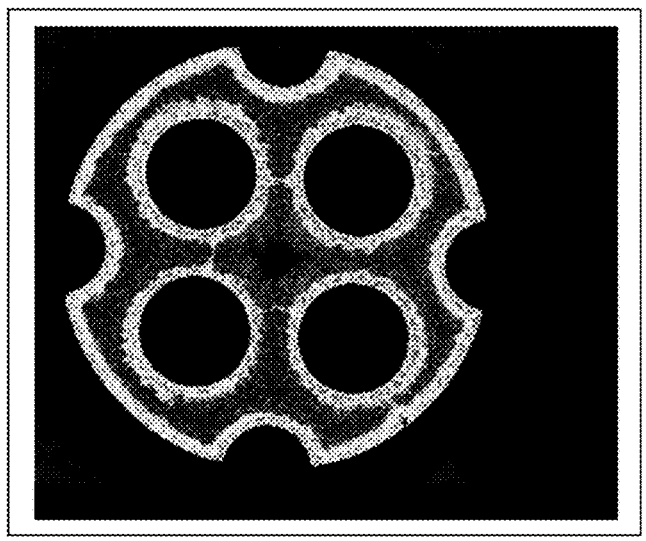
Figure 3

CATALYST PREPARATION METHOD

CROSS-REFERENCE TO RELATED APPLICATIONS

This application is a divisional of U.S. application Ser. No. 13/318,273 filed Jan. 17, 2012, which is a U.S. National Phase application of PCT International Application No. PCT/GB2010/050624, filed Apr. 15, 2010, and claims priority of British Patent Application No. 0907539.1, filed May 1, 2009, the disclosures of which are incorporated herein by reference in their entireties for all purposes.

FIELD OF THE INVENTION

This invention relates to a method of preparing catalysts supported on calcium aluminate.

Calcium aluminate-supported catalysts are used in a number of industrial processes, including methanation and steam reforming processes, such as pre-reforming, primary reforming and secondary reforming. In such cases the catalytically-active metal is typically nickel, but other transition metals or precious metals, may also be used.

In methanation and steam reforming processes, pellets comprising nickel oxide on alumina or calcium aluminate are typically installed and the reduction of the nickel oxide to the active elemental nickel carried out in-situ.

U.S. Pat. No. 4,707,351 describes steam-reforming catalysts made of a low-silica calcium aluminate cement composition in a saddle configuration. The catalysts were prepared by mixing calcium aluminate with water and polyvinylacetate, stamping shapes from the resulting material, drying and calcining the saddles at up to 1400° C. before impregnation with nickel nitrate. The impregnated saddles were further dried and calcined to generate the catalyst precursor. In this process, the calcium aluminate support was hydrated during the shaping process and then calcined to increase its strength and define the micromimetric properties prior to impregnation with nickel nitrate.

Heretofore it has been seen as necessary to impregnate calcium aluminate supports to achieve a uniform dispersion of the metal compound within the pellets such that upon calcination the metal oxide is uniformly dispersed within the pellet, thereby maximising the metal surface area and hence catalyst activity.

BACKGROUND OF THE INVENTION

We have found that by re-hydrating the surface of the calcined shaped calcium aluminate catalyst support and then drying it, the support, once impregnated with a metal compound provides an egg-shell catalyst precursor in which the metal oxide formed upon calcination is concentrated as an outer surface layer on the support and is not uniformly distributed. Moreover, the properties of such catalysts are enhanced in comparison to the known catalysts.

Accordingly, the invention provides a method for preparing a catalyst comprising the steps of:
(i) preparing a calcined shaped calcium aluminate catalyst support,
(ii) treating the calcined shaped calcium aluminate support with water, and then drying the support,
(iii) impregnating the dried support with a solution containing one or more metal compounds and drying the impregnated support,
(iv) calcining the dried impregnated support, to form metal oxide on the surface of the support and
(v) optionally repeating steps (ii), (iii) and (iv) on the metal oxide coated support.

The invention further provides an eggshell catalyst obtainable by the method.

The invention further provides a process for the steam reforming of hydrocarbons comprising the step of contacting a mixture of hydrocarbon and steam at elevated temperature and pressure with the eggshell catalyst.

SUMMARY OF THE INVENTION

By the term "eggshell catalyst" we mean that the catalytically active metal or metals are not uniformly distributed within the catalyst support but are concentrated at the surface and therefore form a thin layer, with the metal or metals being absent beneath this layer. The thickness of the eggshell layer is preferably ≤1000 μm, more preferably ≤800 μm, most preferably ≤300 μm.

The catalyst support is prepared from a calcium aluminate cement. By the term calcium aluminate cement we include those hydraulic cements containing one or more calcium aluminate compounds of the formula $nCaO.mAl_2O_3$ where n and m are integers. Example of such calcium aluminate compounds include calcium monoaluminate ($CaO.Al_2O_3$), tricalcium aluminate ($3CaO.Al_2O_3$), penta calcium trialuminate ($5CaO.3Al_2O_3$), tricalcium penta aluminate ($3CaO.5Al_2O_3$), and dodeca calcium hepta aluminate ($12CaO.7Al_2O_3$). Some calcium aluminate cements, e.g. the so-called "high alumina" cements, may contain alumina in admixture with, dissolved in, or combined with, such calcium aluminate compounds. For example, a well known commercial high alumina cement has a composition corresponding to about 18% calcium oxide, 79% alumina and 3% water and other oxides. This material has a calcium:aluminium atomic ratio of about 1:5, i.e. $2CaO.5Al_2O_3$. Calcium aluminates are often contaminated with iron compounds, but these are not believed to be detrimental to the present invention. Suitable cements include the commercially available Ciment Fondu, and Secar 50, Secar 71, Secar 80 available from Kemeos and CA-25, CA-14, CA-270 available from Almatis.

The support composition employed in the present invention preferably has a calcium:aluminium atomic ratio within the range 1:3 to 1:12, more preferably 1:3 to 1:10, most preferably 1:4 to 1:8. Where the calcium aluminate cement is a "high alumina" cement, no additional alumina may be necessary but, in general, the support is desirably made from a calcium aluminate cement to which an additional amount of alumina, which may be in the form of a transition alumina, monohydrate or trihydrate, has been added.

To accelerate setting, an amount of lime (CaO), e.g. up to 15% by weight of the composition, may also be incorporated into the support composition.

Hence the support will usually be a refractory composition consisting of a calcined mixture of alumina, one or more of said calcium aluminate compounds and optionally lime.

Other oxidic materials, e.g. titania, zirconia or lanthana, may be present in the calcium aluminate support composition. While silica may in some cases be incorporated, for use as a steam reforming support, a low silica content, i.e. less than 1% by weight, preferably less than 0.5% by weight, based on the weight of the oxidic material in the support composition is desirable, as silica has an appreciable volatility under steam reforming conditions. The support composition preferably contains ≤25% by weight, more preferably ≤15% by weight, most preferably ≤10% by weight of oxidic material other than calcium aluminate and alumina.

The shaped catalyst support may be made by forming a calcium aluminate cement powder, optionally with additional alumina and/or lime, into the desired shape, curing the cement and subsequently calcining the shaped support.

Processing aids, such as graphite and/or a metal stearate (e.g. Mg or Al stearate), may be incorporated into the composition prior to shaping: typically the proportion of graphite is 1 to 5% by weight of the composition. The amounts of metal stearate included may be in the range 0.1 to 2.0% by weight.

A typical composition suitable for pellet formation comprises 30 to 70% by weight of a calcium aluminate cement (comprising 65 to 85% by weight of alumina and 15 to 35% by weight of CaO) mixed with 24 to 48% by weight of alumina, 0 to 15% by weight of lime, and 2 to 5% by weight of graphite.

The composition is desirably shaped into pellets using known techniques, but may also be prepared as extrudates or granules. The length, width and height of such shaped units may be in the range 3-50 mm. The support may be in the form of saddles as described in the aforesaid U.S. Pat. No. 4,707,351 but preferably the support is pressed into pellets in the form of cylinders, which may have one or more through holes, for example as described in WO 2004/014549. More preferably the shaped support is in the form of a cylindrical pellet having between 1 and 12 holes extending there-through, especially 3-10 holes of circular cross section, and optionally between 2 and 20 flutes or lobes running along the length of the pellet. Suitable diameters for such pellets are in the range 4-40 mm and the aspect ratio (length/diameter) is preferably ≤2. A particularly preferred shape is a highly domed cylindrical pellet in the form of a cylinder having a length C and diameter D, which has one or more holes extending therethrough, wherein the cylinder has domed ends of lengths A and B, such that (A+B+C)/D is in the range 0.50 to 2.00, and (A+B)/C is in the range 0.40 to 5.00. Such shapes are described in co-pending WO 2010/029323 A1 and WO 2010/029324 A1. C is preferably in the range 1 to 25 mm and D is preferably in the range 4 to 40 mm.

After shaping, the cement in the shaped catalyst support should be cured and the support dried, typically at under 200° C., and then calcined. Curing of the calcium aluminate cement may take place before or during a drying step, e.g. by spraying or immersing the shaped catalyst support with water prior to drying or by heating the shaped catalyst support under conditions of controlled relative humidity prior to volatilising residual water. Calcination is typically carried out by heating the shaped units to between 500 and 1400° C. in air for between 1 and 16 hours. The catalyst support strength increases, while the porosity and surface area decrease, as the calcination temperature increases. Hence the support calcination should be effected at sufficient temperature to obtain the required mechanical strength but should not be so high that the surface area and porosity are unduly reduced.

The shaped calcined catalyst support preferably has a total surface area, as measured by nitrogen absorption, of 0.5 to 40, particularly 1 to 15, $m^2g^{-1}$, and a pore volume of 0.1 to 0.3 $cm^3 \cdot g^{-1}$, as determined by mercury porosimetry.

Prior to the final calcination, the support may be "alkalised" by impregnation with a solution of an alkali such as potassium hydroxide. This serves to minimise lay down of carbon on the catalyst during steam reforming resulting from high temperature cracking of hydrocarbons and from the reaction of carbon oxides with hydrogen. Alkali oxide, e.g. potash, levels of up to about 5% wt on the calcined support may be used.

In the present invention, prior to impregnation with a metal compound, the calcined shaped calcium aluminate support is subjected to a re-hydration step by treating the support with water. The water is desirably free of salts and is preferably demineralised water or deionised water. Small amounts of organic base or ammonia may be added to the water. The treatment of the shaped calcium aluminate support with water may be by immersion or spraying with water at ambient or elevated temperature. The re-hydration step should be performed for a period sufficient to react the surface of the calcined shaped calcium aluminate support with water. In a preferred embodiment, the treatment with water is by immersing the shaped support in water for a period of between 1 and 120 minutes at a temperature in the range 10-95° C. Using water at a temperature of ≤30° C. has been found to give thinner metal oxide layers, which is advantageous, particularly for small catalysts or catalysts with through-holes. The re-hydration step may be performed at atmospheric or elevated pressure.

Following the treatment of the surface of the calcined support with water, the support is dried to remove the water, preferably to remove the physisorbed water and not the chemisorbed water. Thus the support drying is preferably performed at a temperature in the range 25-250° C., more preferably in the range 50-150° C. at atmospheric or reduced pressure. Drying times may be in the range 1-24 hours depending upon the water content.

Without wishing to be bound by theory, it is believed that the re-hydration and drying steps change the surface chemistry of the calcium aluminate support. Evidence indicates that the pores in the surface of the support are not blocked; rather that the surface basicity of the support is affected so that upon impregnation, insoluble compounds of the metal impregnate precipitate at/near the surface of the support thereby generating the eggshell catalyst.

The re-hydrated and dried catalyst support is then impregnated with a solution comprising one or more soluble metal compounds. The impregnation solution preferably comprises one or more transition metals, preferably one or more selected from the group consisting of chromium, manganese, nickel, cobalt, iron, copper and zinc. More preferably the impregnation solution comprises one or more of nickel, cobalt, iron or copper, most preferably nickel.

Aqueous impregnation solutions are particularly suitable. The impregnation solution preferably comprises one or more acidic compounds, i.e. compounds that dissolve in water to give acidic solutions (i.e. the impregnation solution desirably has a pH<7.0). Suitable acidic metal compounds include metal nitrate, metal acetate metal citrate and metal oxalate. Where the impregnated metal is nickel, the metal compound used to impregnate the support is preferably nickel nitrate or nickel acetate.

The concentration of metal in the impregnating solution is desirably in the range 100-300 g metal/liter.

Impregnation may be performed at ambient or elevated temperature and at atmospheric or elevated pressure using known techniques, including immersion of the re-hydrated and dried catalyst support in a metal-containing solution or by so-called "incipient wetness" impregnation where the volume of solution used equates approximately to the pore volume of the support material. Impregnation of the metal compound at ambient temperature (i.e. 10 to 25° C.), and at atmospheric pressure (about 1 bar abs) may be used, however it has been found that by impregnating the support at temperatures in the range 50-90° C., improved control over the thickness of the eggshell layer may be obtained. For example, the eggshell layer thickness on pelleted materials may be ≤800 μm at 20-30° C., but impregnation at 50-90° C. can produce thicknesses of ≤300 μm.

Following impregnation, the impregnated support is dried and calcined. Drying conditions are preferably the same as those used following the re-hydration step. The calcination step to convert the impregnated metal compound to its corresponding metal oxide is preferably performed in air at a temperature in the range 250-850° C. An advantage of the present invention, by virtue of the lower metal content and the increased metal concentration at the surface of the catalysts, is that the amount of nitrogen oxides evolved during calcination of metal nitrate-based precursors can be reduced compared with current catalyst materials.

The catalytic metal content of the resulting catalyst may be determined by a number of factors such as the metal content of the solution and the impregnation conditions. Steam reforming catalysts formed by impregnation typically have a NiO content in the range 10-35% wt. Precipitated pre-reforming catalysts can have NiO contents of 40-80% wt or more. Methanation catalysts typically have a NiO content in the region of 30-35% wt. In the present invention, because the catalytic metal oxide is concentrated at the surface of the support it is possible to achieve improved catalyst activity with reduced metal loadings. This has clear commercial benefits. The catalytic metal oxide content of the calcined catalyst is preferably in the range 2-25% wt, preferably 4-15% wt. Thus one impregnation may be sufficient to generate the desired catalyst. However if desired, the re-hydration, drying and impregnation steps may be repeated until the metal oxide content of the calcined material is above 2.5% wt, preferably above 5% wt, more preferably above 7.5% wt, most preferably above 10% wt. Multiple impregnations may be performed using the same or different catalytically active metal. In order to maintain the eggshell catalyst, the metal oxide containing support should be re-hydrated, dried and calcined prior to each metal impregnation.

The specific surface area of the catalytic metal is suitably in the range 0.1 to 50 m²/g of catalyst. Within this range, larger areas are preferred for reactions under 600° C.

One or more promoter compounds may be impregnated into the dried support and/or the metal oxide coated support. Hence one or more promoter compounds may be included in the metal impregnating solution or the promoter may be added subsequently by a separate impregnation. The promoter may be confined to the eggshell layer or may be distributed throughout the catalyst support. Promoters include precious metals such as platinum, palladium, iridium, ruthenium, rhodium and gold. Lanthanide metals such as lanthanum and cerium may also be included as promoters. Water-soluble salts, particularly nitrates, may be used as sources of the metal promoters. More than one promoter may be present and additional alkali may also be added. The amount of promoter metal will typically be in the range 0.1-5% wt on the calcined catalyst material.

The catalysts may be provided and used in their oxidic form. E.g. oxidic Co catalysts may be used for oxidation reactions.

Where the catalyst comprises a reducible metal such as Cu, Ni, Co or Fe, the calcined product may be provided in its oxidic form and reduction of the metal oxide, if required, to form elemental metal carried out in-situ, i.e. in the reactor in which the catalyst is to be used, with a hydrogen-containing gas. Known reduction techniques may be used.

Alternatively, the oxidic catalyst may be reduced ex-situ and then the elemental metal coated with a thin passivating layer of oxide using an oxygen containing gas. In this way the catalyst may be transported safely to the user, and the reduction time to generate the active catalyst and quantity of hydrogen used during the subsequent activation, reduced. This has clear benefits for the user. Therefore in one embodiment, the method for preparing the catalyst further comprises the steps of reducing a reducible metal oxide to elemental form with a hydrogen-containing gas mixture and subsequently passivating the surface of the elemental metal with an oxygen-containing gas. Oxygen and carbon dioxide gases may be used for example as described in U.S. Pat. No. 4,090,980.

The eggshell catalysts prepared according to the invention may be used in steam reforming processes such as primary steam reforming, secondary reforming of a primary reformed gas mixture and pre-reforming. The catalysts may also be used for methanation reactions, hydrogenation reactions and, in oxidic unreduced form, for the decomposition of hypochlorite in aqueous solutions.

In steam reforming, a hydrocarbon, typically a methane-containing gas such as natural gas or naphtha is reacted with steam and/or, where appropriate, carbon dioxide, over a catalytically active material, often comprising nickel, to produce a gas containing hydrogen and carbon oxides. The hydrogen producing reactions are:

$$CH_4 + H_2O \leftrightarrow CO + 3H_2$$

$$"CH_2" + H_2O \rightarrow CO + 2H_2$$

("CH2" represents hydrocarbons higher than methane, for example normally gaseous hydrocarbons and normally liquid hydrocarbons boiling at up to 200° C.). The analogous reactions with carbon dioxide can be carried out separately or with the steam reaction.

$$CH_4 + CO_2 \rightarrow 2CO + 2H_2$$

$$"CH_2" + CO_2 \rightarrow 2CO + H_2$$

These reactions are strongly endothermic and the process is especially suitable when they are carried out with external heating as in tubular steam reforming. Alternatively the heat can be supplied by heating the reactants and passing steam over the catalyst in an adiabatic bed or in a hybrid process in which oxygen is a reactant, so that heat evolved in oxidation is absorbed by the endothermic reactions. The hybrid process can be applied to the product of the tubular or adiabatic process that is, in "secondary reforming", or to fresh feedstock ("catalytic partial oxidation" or "autothermal reforming"). Commonly these reactions are accompanied by the water-gas shift reaction:

$$CO + H_2O \leftrightarrow CO_2 + H_2$$

If the starting hydrocarbon is "CH₂" and the temperature is relatively low, the methanation reaction (exothermic) may also occur.

$$CO + 3H_2 \rightarrow CH_4 + H_2O$$

$$CO_2 + 4H_2 \rightarrow CH_4 + 2H_2O$$

However, the steam reforming process is operated preferably in net endothermic conditions and the hydrogen containing gas produced contains at least 30% v/v of hydrogen on a dry basis. Preferably it contains less than 30, especially less than 10, % v/v of methane on a dry basis. For the production of hydrogen-containing synthesis gas, the outlet temperature is preferably at least 600° C. to ensure low methane content. While the temperature is generally in the range 750-900° C. for making synthesis gas for ammonia or methanol production, it may be as high as 1100° C. for the production of metallurgical reducing gas, or as low as 700° C. for the production of town gas. For the hybrid process using oxygen, the temperature may be as high as 1300° C. in the hottest part of the catalyst bed.

In pre-reforming, a hydrocarbon/steam mixture is subjected to a step of adiabatic low temperature steam reforming. In such a process, the hydrocarbon/steam mixture is heated, typically to a temperature in the range 400-650° C., and then passed adiabatically through a fixed bed of a suitable particulate catalyst, usually a catalyst having a high nickel content, for example above 40% by weight. The catalysts may be simple cylinders or a multiholed, lobed shape. Pre-reforming catalysts are typically provided in a pre-reduced and passivated form, although oxidic catalyst may also be installed. During such an adiabatic low temperature reforming step, any hydrocarbons higher than methane react with steam on the catalyst surface to give a mixture of methane, carbon oxides and hydrogen. The use of such an adiabatic reforming step, commonly termed pre-reforming, is desirable to ensure that the feed to the steam reformer contains no hydrocarbons higher than methane and also contains a significant amount of hydrogen. This is desirable in order to minimise the risk of carbon formation on the catalyst in the downstream steam reformer. The pressure in steam reforming processes is typically in the range 1-50 bar abs. but pressures up to 120 bar abs. are proposed. An excess of steam and/or carbon dioxide is normally used, especially in the range 1.5 to 6, for example 2.5 to 5, mols of steam or carbon dioxide per gram atom of carbon in the starting hydrocarbon.

Where the catalyst is to be used for methanation, in order to remove low concentrations of CO and $CO_2$ (0.1-0.5% vol) from a hydrogen-containing gas, the hydrogen-containing gas is typically passed through a particulate fixed bed of a nickel-containing catalyst at a temperature in the range 230-450° C. and pressures up to about 50 bar abs or higher up to about 250 bar abs. Unlike steam reforming the catalyst are preferably simple cylindrical pellets without through holes, although such pellets may be used if desired. Typical pellet diameters are in the range 2.5-6 mm, with lengths in the same range. The catalysts may be provided in oxidic form or pre-reduced and passivated form.

BRIEF DESCRIPTION OF THE DRAWINGS

The invention is also illustrated by reference to the Examples and FIGS. 1-3.

FIG. 1 depicts an image of a cylindrical catalyst pellet cut in two to show an eggshell layer of catalyst prepared according to the present invention;

FIG. 2 depicts an image of a similar catalyst pellet prepared according to the prior art, and FIG. 3 depicts an electron-probe micro-analyser (EMPA) image of a cross section of a lobed 4-hole cylindrical catalyst pellet with an eggshell layer of catalyst prepared according to the present invention.

DETAILED DESCRIPTION OF THE INVENTION

Examples

Example 1. Preparation of a Catalyst Support a) Calcium aluminate cement was blended with alumina trihydrate and lime to obtain a mixture with a Ca:Al ratio of 10:43. Graphite (4 wt %) was added, and the resulting mixture pelleted using a hydraulic tabletting machine to give cylinders of diameter 3.3 mm and length 3.3 mm. The pellets were subjected to water-curing and calcination to obtain a calcined shaped support with the following properties.

BET (Nitrogen): 5.7 $m^2/g$
Pore volume: 0.28 $cm^3/g$
Density: 1.66 g/cc b) The method of Example 1(a) was repeated to produce pellets of diameter 5.4 mm and length 3.0 mm.

c) The method of Example 1(a) was repeated except that calcium aluminate cement was blended with alumina trihydrate to obtain a mixture with a Ca:Al ratio of 10:74.

Example 2. Preparation of a Ni Catalyst a) Re-hydration. The shaped calcined calcium aluminate support from Example 1(b) was treated with water by immersing the pellets in de-mineralised water at 30° C. for 40 minutes. The pellets were removed and dried at 110° C. for 16 hours.

b) Incorporation of Ni. The catalyst support pellets were then immersed in a solution of nickel nitrate in de-mineralised water (200 g Ni/liter) for 5 minutes at 25° C. The impregnated pellets were then removed and allowed to drain for 10 minutes and dried at 110° C. for 6 hours. The dried impregnated pellets were then heated at 100° C./hour to 650° C. and then held at 650° C. for 4 hours to convert the nickel nitrate to nickel oxide. The re-hydrating, drying, impregnating, drying and calcining procedure was repeated on the nickel oxide containing pellets a further two times. The Ni was concentrated in a thin layer around the edge of the catalyst pellet as shown in FIG. 1. The thickness of the eggshell layer is about 800 μm.

The procedure was repeated on the support of Example 1(a), using the same water treatment conditions but carrying out the Ni impregnation each time for 5 minutes at 70° C. instead of 25° C. The weight increase after each calcination was measured on 20 pellets and an average taken. The results were as follows;

| Impregnation | Weight of Support (g) | Weight of oxidic catalyst (g) | NiO weight (g) | NiO loading (% wt) |
| --- | --- | --- | --- | --- |
| 1 | 0.045 | 0.0456 | 0.0009 | 1.974 |
| 2 | 0.045 | 0.0475 | 0.0028 | 5.895 |
| 3 | 0.045 | 0.0485 | 0.0038 | 7.835 |

The final catalyst properties were;
BET (Nitrogen): 43.6 $m^2/g$
Pore volume: 0.17 $cm^3/g$
Density: 1.84 g/cc This material was termed catalyst 2A.

The procedure applied to the support of Example 1(a) was repeated on the support of Example 1(c), using the same water treatment and impregnation conditions. An egg-shell catalyst material was produced.

In comparison, the shaped calcined calcium aluminate support from Example 1(b), but without the above re-hydration step, was immersed in a solution of nickel nitrate in de-mineralised water (200 g Ni/liter) for 5 minutes at 25° C. The impregnated pellets were then removed and allowed to drain for 10 minutes and dried at 110° C. for 6 hours. The dried impregnated pellets were then heated at 100° C./hour to 650° C. and then held at 650° C. for 4 hours to convert the nickel nitrate to nickel oxide. The impregnating, drying and calcining procedure was repeated on the nickel oxide containing pellets a further two times. The Ni was distributed throughout the catalyst pellet as seen in FIG. 2.

As a further comparison, the shaped calcined calcium aluminate support from Example 1(a), again without the re-hydration step, was immersed in a solution of nickel nitrate in de-mineralised water (200 g Ni/liter) for 5 minutes at 70° C. The impregnated pellets were then removed and allowed to drain for 10 minutes and dried at 110° C. for 6 hours. The dried impregnated pellets were then heated at 100° C./hour to 650° C. and then held at 650° C. for 6 hours to convert the nickel nitrate to nickel oxide. The impregnating, drying and calcining procedure was repeated on the nickel oxide containing pellets a further two times. The NiO content of this material after the final calcination was about 16.5 wt %. This comparative material was termed catalyst 2B.

Example 3: Testing

The catalysts 2A and 2B were tested in a laboratory scale steam reformer with a reformer tube internal diameter of 1-inch. The catalysts were diluted with fused alumina chips (sieve fraction 3.35 mm-4.74 mm) and reduced using 50 vol % $H_2$ in $N_2$ at 480° C. for 2 hours. After catalyst reduction, catalyst performance was assessed over the temperature range 480° C. to 750° C. The feed gas was natural gas mixed with steam at a steam:carbon ratio of 3.0:1. The exit gas composition was analysed by infra-red and gas chromatography.

The results were as follows;

| | Catalyst | | |
|---|---|---|---|
| | 2A Ethane conversion (%) | 2B Ethane conversion (%) | Improvement by egg-shelling |
| 600° C. | 77 | 54 | 41% |
| 540° C. | 66 | 43 | 53% |
| 480° C. | 44 | 29 | 50% |
| 670° C. | 83 | 66 | 26% |
| 750° C. | 88 | 76 | 16% |
| 670° C. | 82 | 63 | 31% |

The ethane conversion is better for the eggshell catalyst 2A across the temperature range.

Example 4. Preparation of Catalysts a) Catalyst Support. Calcium aluminate cement was blended with alumina trihydrate and lime to obtain a mixture with a Ca:Al ratio of 10:43. Graphite (4 wt %) was added, and the resulting mixture pelleted using a hydraulic tabletting machine to give cylinders of diameter 5.4 mm and length 5.4 mm. The pellets were subjected to water-curing and calcination to obtain a calcined shaped support with the same properties as example 1(a).

b) Re-hydration. The shaped calcined calcium aluminate support was treated with water by immersing the pellets in de-mineralised water at 30° C. for 40 minutes. The catalyst support pellets were removed from the water and dried at 110° C. for 16 hours.

c) Catalyst Preparation. The catalyst support pellets were immersed in a solution of metal nitrate in de-mineralised water as detailed below for 5 minutes at 25° C.

| Metal nitrate | Concentration (g of metal/100 ml) |
|---|---|
| Co | 10 |
| Cu | 10 |
| Ni | 10 |

The impregnated pellets were then removed and allowed to drain for 10 minutes and dried at 110° C. for 12 hours.

The pellets were analysed by optical microscopy and in each case it was found that the metal compound was concentrated around the edge of the pellet, i.e. that an eggshell material had been formed.

In comparison, the shaped calcined calcium aluminate support, without the re-hydration step (b), was immersed in the solution of metal nitrate in de-mineralised water as detailed above for 5 minutes at 25° C. The impregnated pellets were then removed and allowed to drain for 10 minutes and dried at 110° C. for 12 hours. The pellets were analysed by optical microscopy and in each case the metal was distributed throughout the catalyst.

Example 5. Preparation of Catalyst with Ni Acetate a) Catalyst Support. Calcium aluminate cement was blended with alumina trihydrate and lime to obtain a mixture with a Ca:Al ratio of 10:43. Graphite (4 wt %) was added, and the resulting mixture pelleted using a hydraulic tabletting machine to give cylinders of diameter 5.4 mm and length 5.4 mm. The pellets were subjected to water-curing and calcination to obtain a calcined shaped support with the same properties as example 1(a).

b) Re-hydration. The shaped calcined calcium aluminate support from was treated with water by immersing the pellets in de-mineralised water at 30° C. for 40 minutes. The pellets were removed and dried at 110° C. for 16 hours.

c) Catalyst preparation. The pellets were then immersed in a solution of Ni-acetate (2 g/100 ml) in de-mineralised water for 5 minutes at 25° C.

The impregnated pellets were then removed and allowed to drain for 5 minutes and dried at 110° C. for 4 hours.

The pellet was analysed by optical microscopy and it was found that the nickel was concentrated around the edge of the pellet.

Example 6: Shaped Catalyst Support with Through Holes

A 4-holed, 4-lobed catalyst calcined calcium aluminate catalyst support was prepared according to the method of Example 1. The catalyst support was re-hydrated and impregnated three times at 25° C. with nickel nitrate according to the method of Example 2. Electron-probe microanalysis (EPMA) of a cross section of the resulting dried and calcined catalyst pellet showed a thin layer of nickel oxide (lighter area) around the outside of the pellet and around the circumference of each of the through holes. The EPMA image is depicted in FIG. 3.

The invention claimed is:

1. An eggshell catalyst comprising an outer eggshell layer comprising nickel oxide and having a thickness of 1000 microns or less on the surface of a calcined, shaped calcium aluminate cement support, wherein the nickel oxide is concentrated within the eggshell layer and not uniformly distributed within the calcined, shaped calcium aluminate cement support.

2. The eggshell catalyst of claim 1 wherein the calcium aluminate support comprises calcium aluminate cement powder and at least one of alumina or lime.

3. The eggshell catalyst of claim 1 further comprising an alkali metal oxide.

4. The eggshell catalyst of claim 1 wherein the support is in the form of a shaped pellet or extrudate.

5. The eggshell catalyst of claim 4 wherein the support is in the form of a cylindrical pellet having between 1 and 12 holes extending there-through.

6. The eggshell catalyst of claim 5 wherein the support is in the form of a cylindrical pellet having between 1 and 12 holes extending there-through and between 2 and 20 flutes or lobes.

7. The eggshell catalyst of claim 6 wherein the support has 4 holes extending there-though and 4 lobes.

8. The eggshell catalyst of claim 1 wherein nickel oxide content of the catalyst is in the range of from 2 wt % to 25% wt.

9. The eggshell catalyst of claim 1, wherein the outer eggshell layer comprising nickel oxide has a thickness of 800 microns or less.

10. The eggshell catalyst of claim 1, wherein the outer eggshell layer comprising nickel oxide has a thickness of 300 microns or less.

11. The eggshell catalyst of claim 4, wherein each of the length, width, and height of the shaped pellet or extrudate is in the range of from 3 mm to 50 mm.

12. The eggshell catalyst of claim 5, wherein the cylindrical pellet has a diameter in a range of from 4 mm to 40 mm, and an aspect ratio of length to width of 2 or less.

13. An eggshell catalyst comprising an outer eggshell layer of nickel oxide having a thickness of 1000 microns or less on the surface of a calcined, shaped calcium aluminate cement support, the eggshell catalyst precursor obtained by a method comprising:
  (i) preparing a calcined shaped calcium aluminate catalyst support by forming a calcium aluminate cement powder, optionally with additional alumina and/or lime, into a desired shape, curing the cement and subsequently calcining the shaped support; then
  (ii) treating the calcined shaped calcium aluminate support with water, said water being essentially free of salts, and drying the support; then
  (iii) impregnating the dried support with the solution containing one or more nickel compounds and drying the impregnated support; then
  (iv) calcining the dried impregnated support, to form the outer eggshell layer of nickel oxide on the surface of the support; and
  (v) optionally repeating steps (ii), (iii) and (iv);
  so as to form the eggshell catalyst precursor.

14. An eggshell catalyst obtained by subjecting the eggshell catalyst of claim 13 to a reducing environment, so as to produce an outer eggshell layer having a thickness of 1000 microns or less on the surface of a calcined, shaped calcium aluminate cement support, the outer eggshell layer comprising elemental nickel.

15. The eggshell catalyst of claim 14, wherein the reducing environment comprises hydrogen.

16. An eggshell catalyst obtained by subjecting the eggshell catalyst of claim 14 to a oxygen environment, so as to provide a passivating layer of nickel oxide on the elemental nickel.

17. An eggshell catalyst comprising an outer eggshell layer comprising elemental nickel and having a thickness of 1000 microns or less on the surface of a calcined, shaped calcium aluminate cement support, wherein the elemental nickel is concentrated within the eggshell layer and not uniformly distributed within the calcined, shaped calcium aluminate cement support.

18. The eggshell catalyst of claim 17, wherein the elemental nickel further comprises a passivating layer of nickel oxide.

\* \* \* \* \*